(12) United States Patent
Miller et al.

(10) Patent No.: US 9,924,858 B2
(45) Date of Patent: Mar. 27, 2018

(54) LARYNGOSCOPE

(71) Applicant: INTERSURGICAL AG, Vaduz (LI)

(72) Inventors: Andrew Neil Miller, Wokingham (GB); Laura Elizabeth Breckon, Workingham (GB)

(73) Assignee: Intersurgical AG, Vaduz (LI)

( * ) Notice: Subject to any disclaimer, the term of this patent is extended or adjusted under 35 U.S.C. 154(b) by 15 days.

(21) Appl. No.: 14/364,027

(22) PCT Filed: Dec. 10, 2012

(86) PCT No.: PCT/EP2012/074938
§ 371 (c)(1),
(2) Date: Jun. 9, 2014

(87) PCT Pub. No.: WO2013/083836
PCT Pub. Date: Jun. 13, 2013

(65) Prior Publication Data
US 2014/0371536 A1    Dec. 18, 2014

(30) Foreign Application Priority Data
Dec. 9, 2011    (GB) .................................. 1121191.9

(51) Int. Cl.
*A61B 1/267* (2006.01)
*A61B 1/06* (2006.01)
(Continued)

(52) U.S. Cl.
CPC ................ *A61B 1/267* (2013.01); *A61B 1/06* (2013.01); *B29C 45/0053* (2013.01);
(Continued)

(58) Field of Classification Search
CPC ........... A61B 1/267–1/2676; A61B 1/06–1/07; B29K 2021/00–2021/006
(Continued)

(56) References Cited

U.S. PATENT DOCUMENTS 3,598,113 A    8/1971    Moore et al.
5,261,392 A    11/1993    Wu
(Continued)

FOREIGN PATENT DOCUMENTS

WO    2004071285 A1    8/2004
WO    2011141749 A1    11/2011

OTHER PUBLICATIONS

Great Britain Search Report for GB1121191.9, filed Dec. 9, 2011 (dated Aug. 13, 2012) (4 pages).
(Continued)

*Primary Examiner* — Jacqueline Johanas
(74) *Attorney, Agent, or Firm* — LeClairRyan, a Professional Corporation

(57)    ABSTRACT

A laryngoscope (10) is disclosed, the laryngoscope (10) comprising a unitary body (11) formed of a first material and having portions shaped to define a handle (18) and a blade (28) of the laryngoscope (10), the body (11) having a recess (44) therein shaped to receive one or more electrical components (12,13,14,15) for operation of a light mounted in the blade portion (28), wherein blade (28) comprises a first surface (32) which faces away from the handle portion (18); and a cover material (17) molded over a portion of the first surface (32), said cover material (17) being softer than the first material so as to provide a resilient portion (17) which can be pressed against a patient's teeth during use of the laryngoscope (10).

20 Claims, 3 Drawing Sheets

(51) Int. Cl.
  *B29C 45/00* (2006.01)
  *B29C 45/16* (2006.01)
  *B29K 21/00* (2006.01)
  *B29K 23/00* (2006.01)
  *B29L 31/00* (2006.01)

(52) U.S. Cl.
  CPC .... *B29C 45/1676* (2013.01); *B29K 2021/003* (2013.01); *B29K 2023/12* (2013.01); *B29K 2995/007* (2013.01); *B29L 2031/753* (2013.01); *F04C 2270/041* (2013.01)

(58) Field of Classification Search
  USPC .................. 362/189, 200, 201, 205, 206
  See application file for complete search history.

(56) References Cited

U.S. PATENT DOCUMENTS

| | | | |
|---|---|---|---|
| 5,277,173 A | 1/1994 | Cantele | |
| 5,438,976 A | 8/1995 | Nash | |
| 5,879,304 A * | 3/1999 | Shuchman et al. | 600/193 |
| 6,106,126 A * | 8/2000 | Neustadt | G09F 13/04 362/20 |
| 6,428,180 B1 * | 8/2002 | Karram et al. | 362/119 |
| 6,569,089 B1 * | 5/2003 | Covington | A61B 1/0669 600/199 |
| 7,044,910 B2 | 5/2006 | Cartledge et al. | |
| 7,182,487 B1 * | 2/2007 | Pickard | F21V 15/01 174/535 |
| 7,631,981 B2 * | 12/2009 | Miller et al. | 362/119 |
| 7,771,350 B2 * | 8/2010 | Geist et al. | 600/199 |
| 7,878,973 B2 * | 2/2011 | Yee et al. | 600/199 |
| 7,946,981 B1 | 5/2011 | Cubb | |
| 7,988,622 B2 * | 8/2011 | Achas Gandarias | 600/188 |
| D724,208 S * | 3/2015 | Miller et al. | D24/137 |
| 2004/0189444 A1 * | 9/2004 | Gill | 340/309.16 |
| 2005/0240081 A1 | 10/2005 | Eliachar | |
| 2006/0189847 A1 * | 8/2006 | Yee et al. | 600/199 |
| 2007/0235040 A1 * | 10/2007 | Salcedo et al. | 128/859 |
| 2009/0097236 A1 * | 4/2009 | Miller et al. | 362/119 |
| 2010/0228098 A1 * | 9/2010 | Raghuprasad | A61B 3/112 600/300 |
| 2011/0077466 A1 * | 3/2011 | Rosenthal | 600/188 |
| 2011/0196203 A1 * | 8/2011 | Xiao et al. | 600/120 |
| 2011/0201890 A1 * | 8/2011 | Rosenthal | 600/188 |
| 2012/0134135 A1 * | 5/2012 | Richmond | F21V 21/0824 362/85 |
| 2013/0060090 A1 * | 3/2013 | McGrath et al. | 600/188 |
| 2014/0371536 A1 * | 12/2014 | Miller et al. | 600/195 |

OTHER PUBLICATIONS

Great Britain Supplemental Search Report for GB1121191.9, filed Dec. 9, 2011 (dated Jan. 8, 2013) (2 pages).

PCT International Search Report and Written Opinion for PCT/EP2012/074938, filed Dec. 10, 2012 (dated Apr. 26, 2013) (14 pages).

* cited by examiner

LARYNGOSCOPE

This application is a national stage application under 35 U.S.C. § 371 of PCT Patent Application Serial No. PCT/EP2012/074938, filed Dec. 10, 2012, which claims the priority benefit of Great Britain Application No. 1121191.9, filed Dec. 9, 2011.

The present invention relates to a laryngoscope such as may be used, for example, during tracheal intubation of a patient.

One common method of intubation requires the insertion of an endotracheal tube through the mouth of a patient into the trachea. Orotracheal intubation may be required, for example, when it is necessary to mechanically ventilate a patient. It is common practice to use a laryngoscope as a visualisation aid during intubation. Conventional laryngoscopes have a handle and interchangeable blades, which may be curved or straight and which may be provided in a range of sizes to accommodate a range of patients.

Historically, blades and handles have been reusable such that those components can be sterilised between successive uses. However there is a general trend towards disposable products to reduce the risk of infection within medical facilities. An example of a single-use laryngoscope is disclosed in International Publication WO 2004/071285 A1 (International Patent Application No. PCT/AU2004/000159), in which a blade and handle is manufactured as a single component.

One example of a known problem with laryngoscopes is the possibility of causing dental injury when the rigid blade body is pressed against a patient's teeth in order to prise open the mouth. An example of a laryngoscope which is intended to reduce the likelihood of such injuries is disclosed in United States Patent Application Publication US 2004/0034281 A1. That product comprises a soft and pliable insert for the blade so as to reduce the risk of trauma to the patient. The insert is interchangeable between uses such that the main body of the blade and/or handle is reusable with different inserts.

However the shift towards disposable laryngoscopes requires closer control of manufacturing costs in order to provide a viable, ongoing solution for a medical facility or organisation. Accordingly certain functional attributes of a disposable product can become compromised in order to accommodate a simple and cost-effective product design.

It is an aim of the present invention to provide a cost-effective, typically disposable, laryngoscope with improved functional attributes.

According to the present invention, there is provided a laryngoscope comprising a unitary body formed of a first material and having portions shaped to define a handle and a blade of the laryngoscope, the body having a recess therein shaped to receive one or more electrical components for operation of a light source mounted in the blade portion, wherein the laryngoscope further comprises a cover material moulded over the recess in the body so as to irreversibly seal the one or more electrical components therein.

The over-moulding of the recess is particularly advantageous in that it seals the recess so as to prevent ingress of fluids, such as a patient's saliva, or other foreign materials, in a manner which prevents access by the end user without destruction of the device. Accordingly it provides a temper-evident means to ensure the intended single-use nature of the device is not compromised by an end user.

The recess may be formed in the blade portion of the body. The recess may be formed in a side wall of the body, such as a side wall of the blade portion.

The blade portion may have an upper wall or surface which faces away from the handle portion and a pair of opposing side walls or surfaces disposed between the upper wall and the handle. Any, or any combination, of the upper wall and side walls may be elongate in form and may be arcuate and/or tapered in form. The upper wall and side walls may extend from a first blade end at which the blade portion adjoins the handle portion towards a free end or tip portion of the blade.

Additionally or alternatively, the cover may extend over a portion of the upper wall of the blade portion. The cover may cover a region of the upper wall in the vicinity of the first blade end. The cover may extend part way along the length of the upper wall, such as for example less than one half of the length along the blade. The cover may comprise a unitary piece moulded over a side wall and upper wall of the blade portion. The blade portion may comprise a depression in the upper surface such that it is shaped to receive the moulded cover. Thus the cover surface may be flush with an adjacent portion of the upper blade surface.

The material of the cover may be softer than that of the body. The cover may provide a resilient region of the blade, in contrast to the more rigid body of the laryngoscope, which can be located in use against the teeth of a patient in use. Thus the cover can be considered to provide bite region or bite strip. Such a feature can help reduce the likelihood of damage to a patient's teeth in use whilst accommodating a cost-effective, single-use device.

The cover may be arranged such that it is not load-bearing in use. The cover may comprise an over-moulding.

The electrical component may comprise a battery. The electrical component may comprise one or more wires which may extend along an internal cavity of the blade portion between the recess and the light source. The electrical component may comprise a switch. The electrical component may comprise a circuit board and may comprise one or more electronic components.

In one embodiment, the laryngoscope may comprise a closure member, which may be formed of the first material or another rigid material. The closure member may be shaped to cover the recess. The cover may be moulded over the closure member and a portion of the body. The electrical component(s) may be received by the closure member. The closure member may be concave in form at least in the vicinity of the electrical component(s) and may be shaped to define a recess which opposes the recess of the body.

The closure member and/or body may have one or more projecting formations arranged to extend into the recess so as to engage the electrical components. The projecting formations may hold the electrical components in place within the recess.

The closure member may be shaped to define both a portion of the handle and a portion of the blade. The closure member may extend part way along the handle and part way along the blade. The closure member may extend part way along a side wall of the blade portion. The body and closure member may be correspondingly shaped. The closure member may be received within the periphery of the body.

The light source may be provided in a side wall of the blade portion which opposes the side wall in which the cover and/or closure member is provided.

The switch and/or battery may be mounted within a locating formation within the closure member. A first locating formation may be provided for the battery and a second locating formation may be provided for the switch. The switch may comprise a switch housing and a button, such as a push-button, depending therefrom.

The body and/or closure may comprise an opening through which the switch button is accessible to the user. The switch may be mounted such that the switch is recessed with respect to the opening at least when it is in an actuated condition. This may help to prevent accidental actuation of the light and may require a user's digit to be pressed slightly into the opening in order to actuate the switch. The opening may comprise a portion of the recess or else a separate opening. The opening may be provided on the handle or blade, for example towards the first end of the blade or else towards a region of the handle which is adjacent or adjoins the blade. The opening may comprise a port.

The closure may be shaped to provide a portion, such as half, of the opening and the body may be shaped to provide an opposing portion, such as half, of the opening. Those portions may have corresponding wall portions which are brought together during assembly of the laryngoscope so as to define the perimeter of the opening.

The electrical component(s) may be mounted in the closure member and may be held against the body.

The handle may be substantially hollow.

According to a second aspect of the invention, there is provided a laryngoscope comprising a unitary body formed of a first material and having portions shaped to define a handle and a blade of the laryngoscope, the body having a recess therein shaped to receive one or more electrical components for operation of a light source mounted in the blade portion, wherein blade comprises a first surface which faces away from the handle portion and the laryngoscope further comprises a cover material moulded over a portion of the first surface, said cover material being softer than the first material so as to provide a resilient portion which can be pressed against a patient's teeth during use of the laryngoscope.

The blade portion may have a first wall and a pair of opposing side walls disposed between the first wall and the handle. The cover material may be moulded over a portion of both the first wall and at least one side wall. The cover material may be moulded over the recess in the body, for example in the side wall of the blade portion, so as to enclose or encase the electrical components therein.

The cover may extend over a region of the first wall in the vicinity of a first end of the blade. The cover may extend part way along the length of the first wall, such as for example less than one half of the length along the blade. The cover may comprise a unitary piece moulded over a side wall and the first wall of the blade portion.

According to a third aspect of the invention, there is provided a method of manufacturing a laryngoscope comprising moulding a first material so as to define unitary blade and handle portions of the laryngoscope, the body having a formation for receiving a light source and a recess, inserting one or more electrical components for operation of the light source into the recess and moulding a second material over the recess so as to irreversibly seal the electrical component therein.

The moulding of the second material may provide an outer cover for a portion of the body. The second material may be softer than the first material. The second material may be moulded over a first surface of the blade which faces away from the handle portion. Such a cover may provide a bite-strip. The moulding of the second component may comprise an overmoulding step or else a further shot of a multi-shot moulding process The electrical component(s) may be mounted on a closure member which is arranged to cooperate with the recess of the body. The closure member may be mounted against the body portion prior to overmoulding with the second material.

The closure member may be moulded from the same material and/or at the same time as the body. The body and closure may be formed by injection moulding and may be co-formed in different cavities within a mould tool within a single moulding step.

According to a fourth aspect of the invention, there is provided a method of manufacturing the laryngoscope of the second aspect.

Any of the preferable features described above in relation to the first aspect may be applied to any further aspect wherever practicable.

Workable examples of the invention are described in further detail below with reference to the accompanying drawings, of which:

The present invention is directed towards a single-use laryngoscope having a light source and the electrical components required for activation of the light source and an over-moulded cover such that the laryngoscope is usable and disposable as a single article.

Although the terms "upper", "lower", "under", "side", "forward" and the like are used in the description of the invention below with reference to the figures, it will be appreciated that the invention is not limited to any specific orientation and, indeed, the orientation of the laryngoscope may change during use. Accordingly, those terms should be construed as being relative terms only with respect to the other features of the laryngoscope within a common frame of reference.

Figure 1:
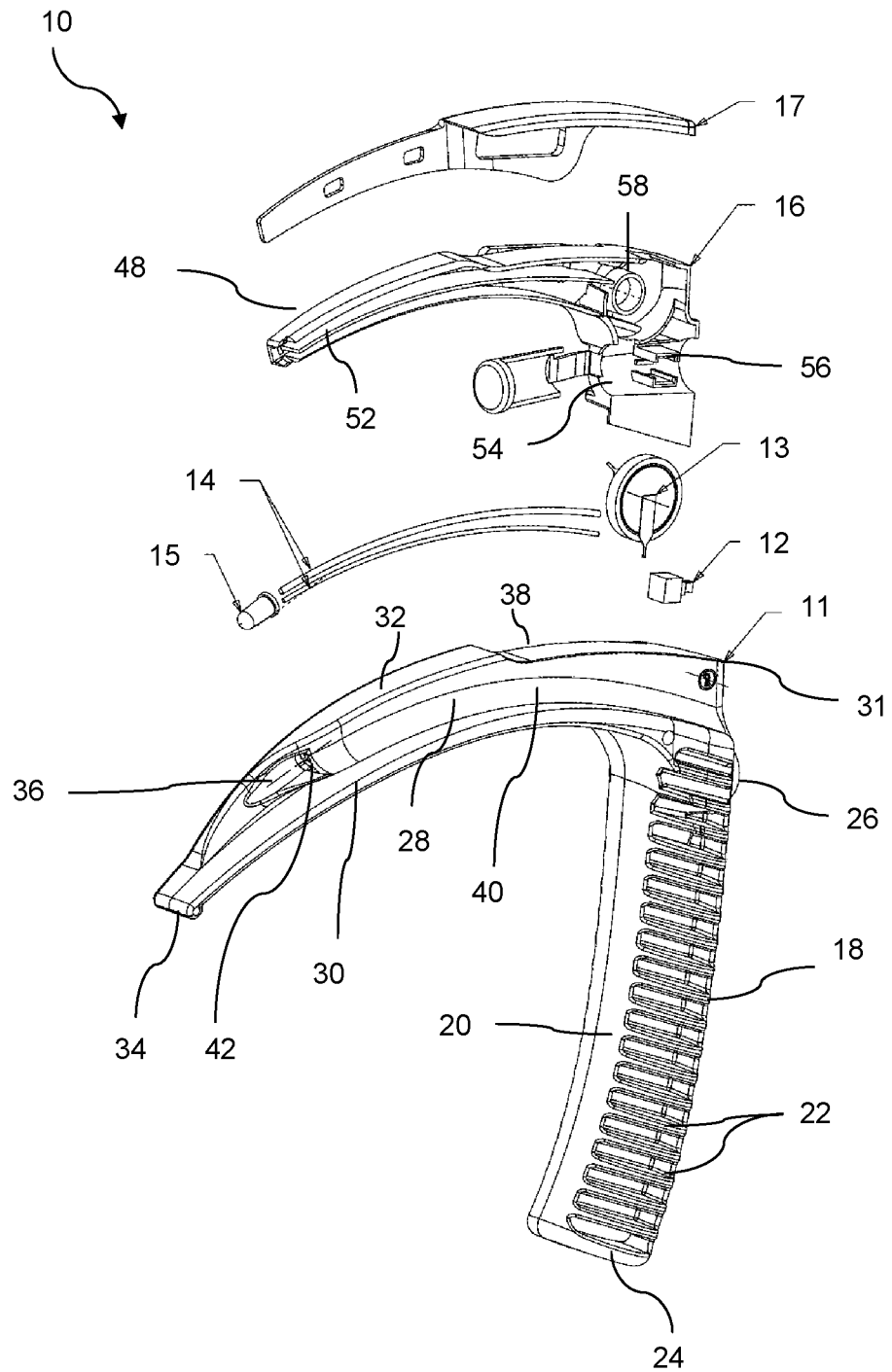
FIG. 1 shows an exploded view of a laryngoscope according to one example of the invention.
Figure 2:
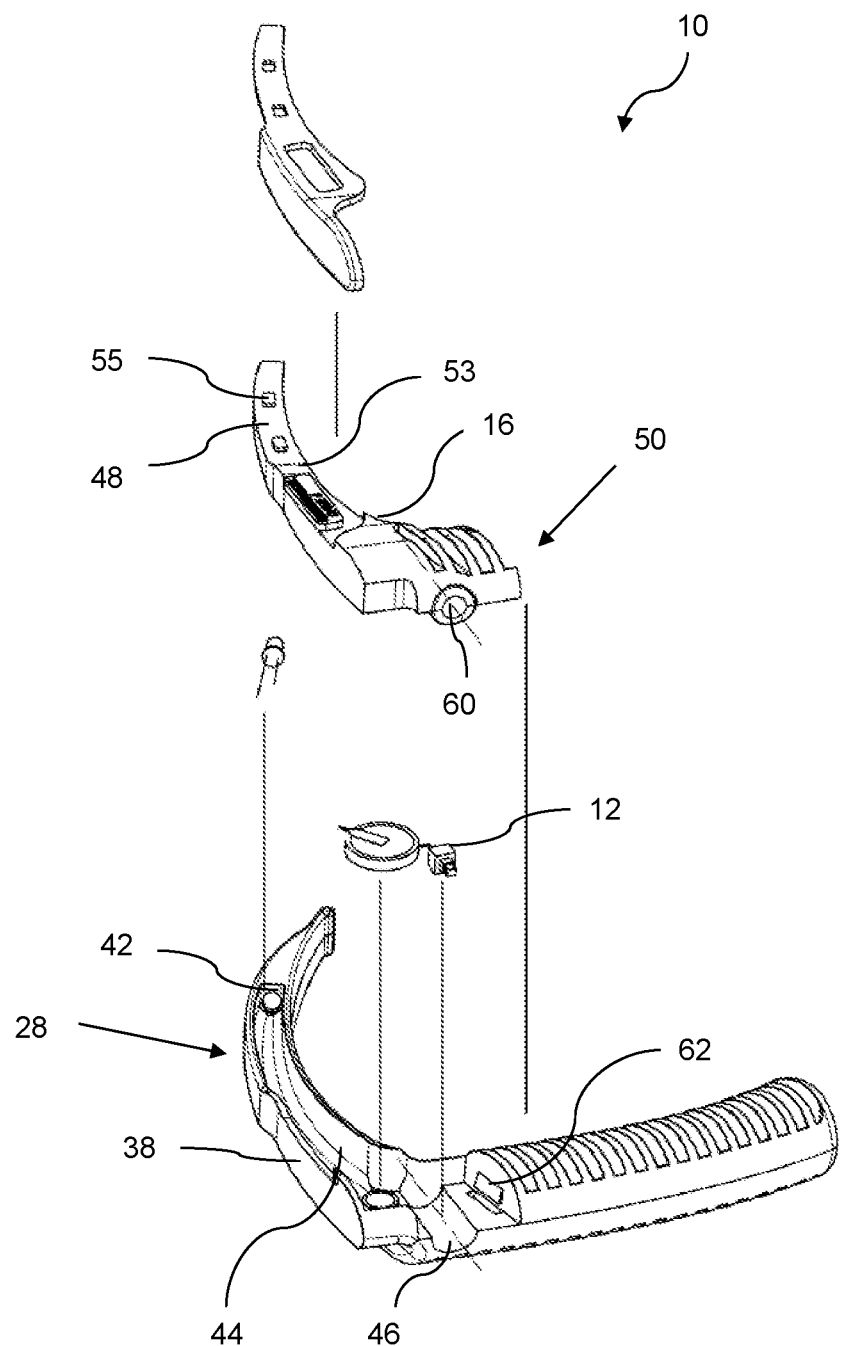
FIG. 2 shows the assembly of the laryngoscope of FIG. 1.

Turning to FIGS. 1 and 2, there are shown the different components making up a laryngoscope according to one example of the invention. The laryngoscope is designated generally as 10 and comprises a body member 11, a switch 12, a battery 13, wires 14, an LED light source 15, a closure member 16 and a cover portion 17.

The body member 11 is of unitary construction which may otherwise be described as being monolithic or uniform to the extent that it is formed as a single piece from a single material. In this example the body material is formed of a plastic material such as polypropylene, which may comprise reinforcing fibres, such as glass fibres to improve its dimensional stability.

The body member 11 comprises a handle section 18 which is elongate in form and generally axial in its structure such that it can be readily gripped for use. The handle 18 comprises an elongate core or spine 20 and a plurality of lateral ridges 22 axially spaced along the spine 20 to provide a grip structure. The plurality of lateral ridges approximate an outer surface of the handle but the spaced arrangement thereof provides for discontinuities there-between which improves the frictional contact with a user's hand when gripped.

The handle section 18 extends from a free end or base 24, at the lower end in FIG. 1, to its opposing end 26, at which it adjoins a laryngoscope blade 28 so as to form an elbow configuration therewith. The angle subtended between the handle 18 and blade 28 is approximately 90° at the elbow, although it can be seen that the blade in this example is arcuate in form and curves towards the handle with distance along the blade length.

The blade 28 has a lower surface or wall 30, which is arcuate in form and faces the handle. In this example, the lower wall is a curved extension of the forward-facing spine portion 20 of the handle such that the interior corner of the elbow between the handle and blade has a fillet.

The exterior corner of the elbow has a rigid projecting corner 31 which is not chamfered. That corner may be substantially right-angled. This provides a useful feature for manipulation of the laryngoscope in use, for example, about which a force can be applied by a user's thumb.

The blade has an upper surface or wall 32 which faces away from the under-surface 30 and handle 18. The upper wall curves in a manner similar to the lower wall 30. However the upper surface curves to a greater degree towards the free end 34 of the blade 28 such that the upper and lower surfaces converge in the vicinity of the blade tip.

Figure 3:
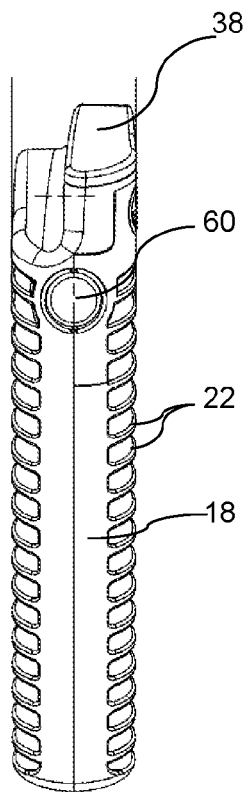
FIG. 3 shows a rear view of the laryngoscope of FIG. 1.
Figure 4:
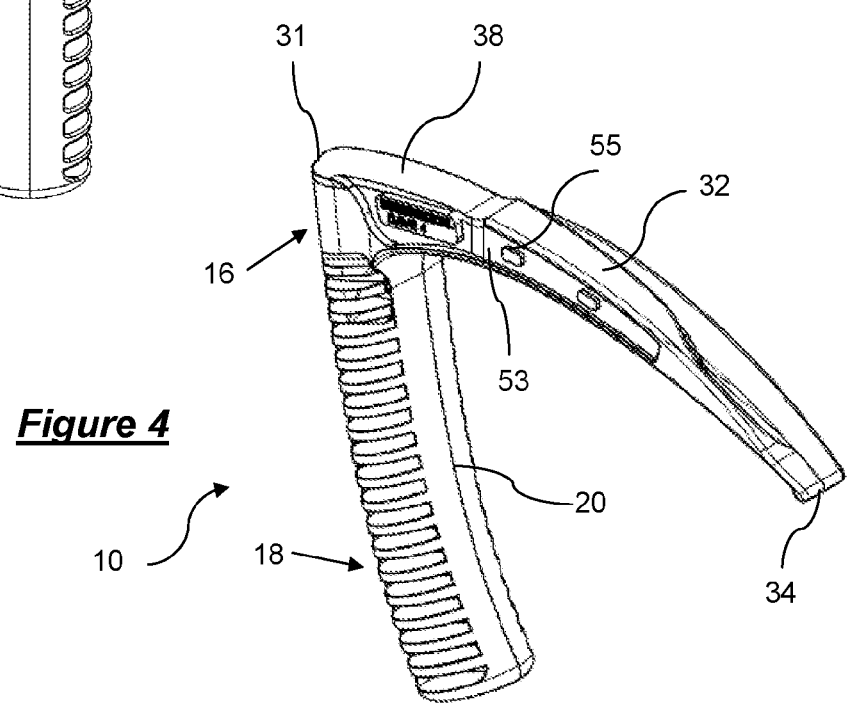
FIG. 4 shows a three-dimensional view of the laryngoscope of FIG. 1.

As can be best seen in FIGS. 2-4, the upper wall is of reduced width compared to the lower wall and spans approximately only half of the width of the laryngoscope. Furthermore the upper surface tapers towards its free end to accommodate a cut-out 36 in one of the side walls as will be described below.

Towards the rear portion, or elbow end, of the upper wall, there is provided a depression 38 in the upper surface, which extends approximately between a quarter and a half of the length of the blade from the corner 31. The depression accommodates the corresponding portion of the cover member 17 as will be described below.

The blade has a lip formation at its free end 34, which is generally rounded or blunt.

In FIG. 1, there is shown an intermediate wall 40, or side wall, which extends between the upper and lower walls. Accordingly the side wall is generally elongate and arcuate in form and is upstanding from the lower wall 30.

The cut-out 36 in side wall 40 has a forward facing wall portion 42 in which there is an aperture for insertion of the LED 15 in a forward facing orientation. This arrangement thus serves as a light mounting/retaining formation.

Turning to FIG. 2, it can be seen that the side of the blade 28 which opposes the side wall 40 is open so as to define an internal cavity or recess 44 within the blade. The cavity 44 is therefore open-sided and provides a partial enclosure defined by the inner faces of the side wall 40, the upper wall 32 and the lower wall 30. The cavity extends from a wider section in the vicinity of the elbow along the blade towards a narrower section in the vicinity of the wall 42.

The cavity also extends into an upper portion of the handle 18. In this regard, one half of an upper section of the handle (i.e. one half of the spine 20 and ridges 22) is cut away so as to provide a rearward facing opening into the cavity 44. A groove 46, which is substantially semi-circular in section, is provided in the exposed upper portion of the handle.

The closure member 16 will now be described with reference to FIGS. 1 and 2 and generally comprises an insert for location within the recess 44 in the body 11. The closure 16 is shaped to closely fit within the cavity 44 and comprises an elongate projection 48 depending from a base portion 50. The elongate projection is arcuate in form and intended to be located within the correspondingly shaped portion of the cavity 44 which extends along the blade. As can be seen in FIG. 1, the projection 48 has an internal baffle or dividing wall 52 along its length.

The closure member 16 has a side wall 53 which closes the recess 44, when the laryngoscope is assembled so as to provide an enclosed internal cavity for the electrical components therein. On an outer surface of the side wall 53, there is provided one or more shallow projections 55, in the form of alignment surfaces or stumps, which allow for engagement, or keying, with the cover 17 as will be described below.

The base portion 50 of the closure member 16 provides an upper portion of the handle 18 when assembled and comprises a plurality of the corresponding ridges on its outer surface.

The base portion 50 also has a groove 54, which is generally semi-circular in section, which corresponds to the groove 46 in the body member 11. As can be seen in FIG. 1, the closure member has inwardly projecting formations depending from its inner surface to assist in the mounting of the components housed therein in use. Those formations comprise a pair of opposing walls 56 for mounting of the switch 12 within the groove 54.

The formations also comprise a pedestal 58 for location of the battery 13. An opposing pedestal formation is provided in the body member recess.

The closure also has peripheral walls which are upstanding from the side wall 54 and which define a partial enclosure for the inner components. Those peripheral walls slot inside the recess walls of the body member during assembly to form a close fitment therewith.

One of the internal walls 56 effectively provides a baffle between a battery housing portion of the closure member 16 and a switch housing portion.

The closure member 16 is of unitary construction which may otherwise be described as being monolithic or uniform to the extent that it is formed as a single piece from a single material. In this example the closure member is formed of a plastic material such as polypropylene, which may comprise reinforcing fibres, such as glass fibres to improve its dimensional stability. The closure member is injection moulded with the body member during manufacture, for example as different cavities within a single tool, or else using two separate mould tools.

Once the body member and closure are formed, the laryngoscope can be assembled by mounting the electrical components on the closure member 16. In this regard, the battery is mounted on the pedestal 58 such that it is a close fit within the peripheral walls of the closure member. The switch 12 is provided as a discrete switch housing which is mounted between formations 56. The LED is mounted at the end of the elongate projection 48 such that the wires extend from the LED along the projection to the battery, where in the wires are spaced by the internal baffle 52. An electrical connection if formed between the battery, switch and wires to allow for activation of the LED in use.

The closure member 16 is then mounted to the body member such that it is a close fit within the cavity 44, wherein the side wall 53 of the closure member then forms a side wall of the laryngoscope and the base portion 50 forms the upper section of the handle. In this example, the handle portion of the body member comprises a projecting or latching formation 62 which engages with a corresponding formation on the handle portion 50 of closure member 16 so as to securely hold the closure in place. The projecting formation 62 may comprise a ramp, which engages with a corresponding indentation in the closure such that the closure member can ride over the ramp in one direction (i.e. for assembly) but is inhibited from disassembly.

When mounted, the groove 46 in the body member and the groove 54 in the closure member are oppposingly aligned so as to form a tubular cavity within the device, in which the switch housing is mounted. The switch is thus recessed with respect to the external wall of the laryngoscope as is accessible via the button 60 provided within the tubular cavity. The button faces rearward, that is in a direction away from the blade, and is mounted at an upper end of the handle 18, for example so that it can be actuated by a user's thumb whilst gripping the handle. The button is arranged such that it is substantially flush with the outer surface of the handle in an inoperative condition and is recessed with respect to the outer surface of the handle when actuated or depressed. This helps to prevent unintentional actuation of the light, for example during storage or transit of the laryngoscope. Also a peripheral wall portion about the button may be raised slightly to further prevent accidental actuation of the button.

The assembled closure and body member are shown in FIGS. 3 and 4.

Once the electrical components have been mounted to the closure member 16 and the closure member has been mounted to the body member 11, the assembled components are over-moulded with the cover material 17. This is achieved by holding the assembled components in a mould tool and injecting the molten cover material into the tool to fill one or more voids within the mould about the assembled components.

In the present example, the depression 38 in the upper surface of the blade becomes covered with the cover material. Also the surface 53 of the closure member is recessed slightly with respect to the side of the body member such that the surface 53 is also over-moulded with the cover material. In this regard the cover 17 can be provided as a unitary piece which extends over the upper surface and at least a portion of the side wall of the laryngoscope blade. Once applied, the cover material forms an outer surface portion of the laryngoscope which is typically flush with an adjacent surface portion of the body and/or closure members. For example, the cover material in the depression 38 has an outer surface which lies substantially flush with the upper surface 32 of the blade.

It is noted that the cover material surrounds the projections 55 in the surface of the closure member and thereby keys with the closure member so as to form a mechanical locking engagement therewith. In this embodiment, the outer surface of each projection 55 is flush with the outer surface of the cover material. Once the cover material has solidified, it is irremovably attached or adhered to both the body member and also the closure member such that it bonds those components together. Also the cover material seals around the fitment between the closure member and the body member so as to seal the electrical components contained within the cavity 44 within the body member. That is to say, the cover material, in its molten state, seals over the abutting portions of (or the interface between) the closure member and the body member.

The cover material comprises a polymer, such as a thermoplastic elastomer, which is softer than the material of the body and closure members. Suitable materials for this purpose may be resilient and/or puncture-resistant under conventional bite forces and may have a Shore A hardness in the region of 70-90. The hardness of the cover may for example be approximately 80 Shore A. In contrast the body material may comprise polypropylene and may be formed of a glass filled polypropylene, which may have a hardness of 70 or more on the Shore D scale.

The depth of the cover material 17 on the upper surface of the blade may be less than 5 mm and, in this embodiment, is approximately 3 mm. The depression 38 is typically of a corresponding depth.

Once assembled in the manner described above, the device provides a single-use, disposable laryngoscope which can be used in a conventional manner by insertion of the tip of the blade into the mouth of a patient and manually applying a force against the patients jaw via the handle so as to urge a patient's mouth open.

It is to be noted that the switch is an on/off switch that can be repeatedly depressed to activate and deactivate the light as required. In another example of the invention, the button may be overmoulded with the cover material and/or may be provided for example in a side wall of the blade. In one embodiment, the button or switch could be actuated by depressing a portion of the cover.

When the laryngoscope blade is urged against the teeth of a patient, for example during intubation, or else to obtain an improved view of the glottis for any other medical purpose, the cover portion on the upper side of the blade cushions the teeth and prevents direct contact with the harder material of the body member. Thus the harder body material provides a rigid spine for the device, whilst the thermoplastic over-moulding of the cover material provides an integral bite or contact strip which is resiliently deformable.

Each laryngoscope is typically individually packaged in a sterile wrapper. The laryngoscope is sufficiently low cost that it can be used for a single procedure and then discarded, removing the need for sterilisation between uses, and thereby reducing the likelihood of infection between patients.

The invention claimed is:

1. A laryngoscope comprising:
   a unitary body formed of a first material and having portions shaped to define a handle and a blade of the laryngoscope, the body having a recess therein receiving one or more electrical components for operation of a light mounted in the blade portion, the blade comprising:
   a first surface which faces away from the handle portion and
   a cover material moulded over a portion of the first surface, said cover material being softer than the first material so as to provide a resilient portion which can be pressed against a patient's teeth during use of the laryngoscope,
   wherein the electrical component comprises a switch, and the laryngoscope further comprises a closure member shaped to cover the recess and shaped to define both a portion of the handle and a portion of the blade, the body and/or closure member comprising an opening through which a switch button is accessible to a user, the switch button being mounted at an upper end of the handle adjacent to the blade wherein the opening is formed by a groove in the closure member and a corresponding groove in the recess, said groove in the recess stretching substantially a diameter of the handle portion.

2. A laryngoscope according to claim 1, wherein the recess is provided in a side wall of the body.

3. A laryngoscope according to claim 2, wherein the side wall of the body in which the recess is provided is a side wall of the blade extending between the first surface and the handle.

4. A laryngoscope according to claim 1, wherein the recess is provided in the blade portion of the body.

5. A laryngoscope according to claim 1, wherein the first surface of the blade is elongate in form and depends from a first end which adjoins the handle to a free end spaced therefrom and the cover material extends part way along the length of the first surface from the vicinity of the first end.

6. A laryngoscope according to claim 1, wherein the cover material is a unitary member which extends over the portion of the first surface and a portion of a side wall of the body.

7. A laryngoscope according to claim 1, wherein the cover material has an outer surface which is substantially flush with an adjacent outer surface of the body.

8. A laryngoscope according to claim 1, wherein the cover material is a thermoplastic elastomer.

9. A laryngoscope according to claim 1, wherein the cover material is adhered to the body.

10. A laryngoscope according to claim 1, wherein the electrical component further comprises a battery and/or one or more wires.

11. A laryngoscope according to claim 1, wherein the cover material is moulded over at least a portion of the closure member.

12. A laryngoscope according to claim 1, wherein the closure member comprises a locating formation for mounting the switch.

13. A laryngoscope according to claim 1, wherein the closure member and body comprise corresponding opposing wall portions which are brought together during assembly of the laryngoscope so as to define a perimeter of the opening for the switch button.

14. A laryngoscope according to claim 13 wherein the opening comprises a port within the handle which faces away from the blade.

15. A laryngoscope according to claim 1, wherein the switch is mounted such that the switch is recessed with respect to the opening at least when it is in an actuated condition.

16. A laryngoscope according to claim 1, wherein the switch is an on/off switch.

17. A laryngoscope according to claim 1, wherein the switch button is integrally formed with the closure member.

18. A laryngoscope according to claim 1, wherein the switch button faces in a direction away from the blade, such that it can be actuated by a user's thumb whilst gripping the handle.

19. A laryngoscope according to claim 1, wherein the closure member defines both a switch mounting and the switch button.

20. A method of manufacturing a laryngoscope according to claim 1 comprising the steps of:
   moulding a first material so as to define the unitary body having blade and handle portions of the laryngoscope;
   moulding a cover material over a portion of the first surface of the unitary body, said cover material being softer than the first material so as to provide a resilient portion which can be pressed against a patient's teeth during use of the laryngoscope; and
   inserting one or more electrical components for operation of the light into the recess.

* * * * *